United States Patent [19]

Bouscary et al.

[11] Patent Number: 5,398,272
[45] Date of Patent: Mar. 14, 1995

[54] COMPRESSION DEVICE FOR RADIOLOGICAL APPARATUS

[75] Inventors: Francois Bouscary, Bourg-la-Reine; Jean-Pierre Saladin, Bagneux, both of France

[73] Assignee: GE Medical Systems, Buc, France

[21] Appl. No.: 148,987

[22] Filed: Nov. 8, 1993

[30] Foreign Application Priority Data

Nov. 10, 1992 [FR] France ............................ 92 13559

[51] Int. Cl.⁶ .............................................. A61B 6/04
[52] U.S. Cl. ...................................... 378/37; 378/208
[58] Field of Search .................... 375/37, 20, 68, 162, 375/163, 164, 177, 178, 180, 208

[56] References Cited

U.S. PATENT DOCUMENTS

| | | | |
|---|---|---|---|
| 4,259,585 | 3/1987 | Novak et al. | 378/37 |
| 4,658,409 | 4/1987 | Summ | 378/37 |
| 4,943,986 | 7/1990 | Barbarisi | 378/37 |
| 5,050,197 | 9/1991 | Virta et al. | 378/37 |
| 5,199,056 | 3/1993 | Darrah | 378/37 |

Primary Examiner—David P. Porta
Attorney, Agent, or Firm—Nilles & Nilles

[57] ABSTRACT

A compression device for a radiological apparatus, the compression device including a compression pad and fastening structure to connect the compression pad to driving elements that are fitted onto the radiological apparatus, wherein both the compression pad and the fastening means are a single unitary piece of injection molded plastic that is substantially transparent to X-rays.

12 Claims, 1 Drawing Sheet

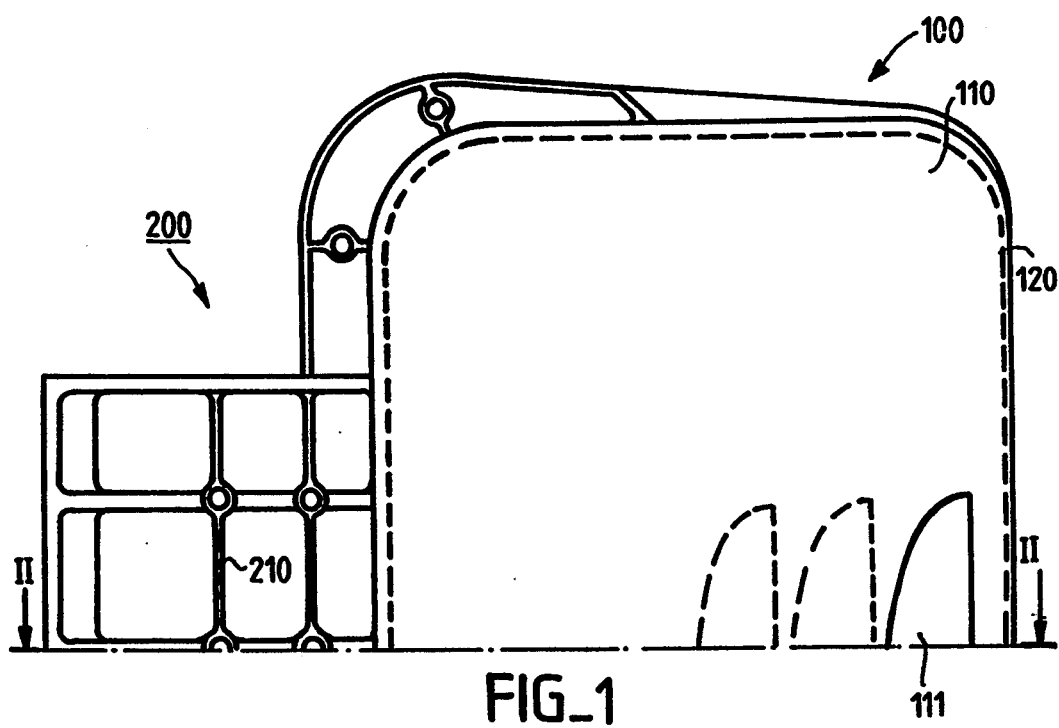
FIG_1
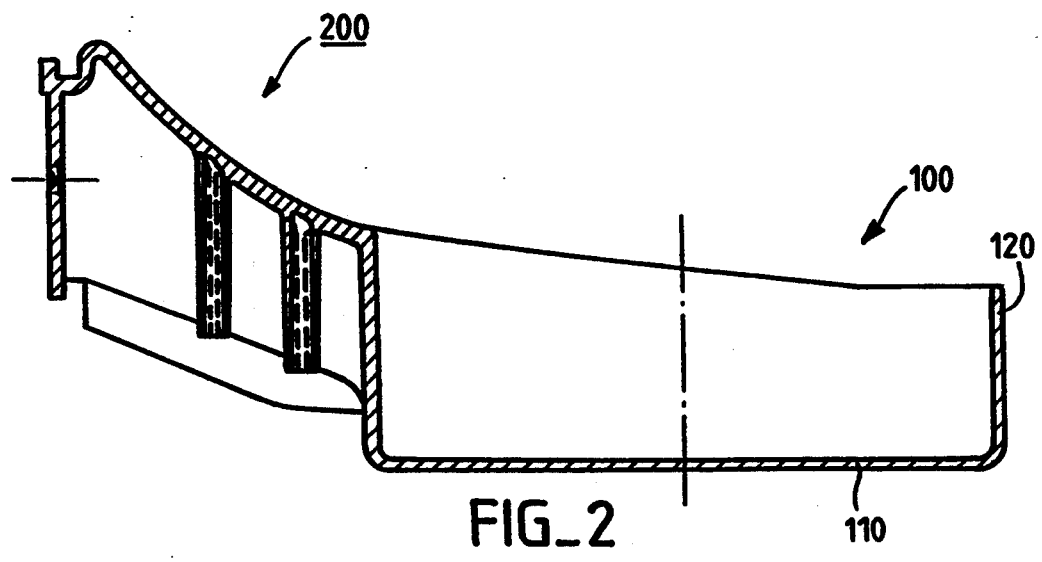
FIG_2

COMPRESSION DEVICE FOR RADIOLOGICAL APPARATUS

BACKGROUND OF THE INVENTION

The present invention relates to a compression device for a radiological apparatus including, a compression pad and means to fasten the compression pad to driving elements fitted on to the radiological apparatus.

The invention can be applied with special advantage in the field of radiological instruments requiring the compression of any organ, notably in the case of mammographies.

At present, the compression devices used in mammography for example, include, a compression means proper, called a compression pad, that comes into contact with the breast to place it in a position where it rests against a plate-holder containing the X-ray sensitive photographic plate. These compression devices also comprise means for fixing the pad to driving elements fitted on to the radiological apparatus, such as a jack or a belt. These driving elements can be used to bring the compression pad to the breast with sufficient pressure of up to $2 \times 10^6$ Pa to ensure that the breast is held satisfactorily against the plate-holder, and also to reduce the thickness crossed by the X-rays so as to limit the dose of radiation received by the patient being examined.

Generally, the compression pad is made of a thermoformed plastic material that is transparent to X-rays. The fastening means are most usually metal elements attached to the plastic pad by screws or equivalent means. Owing to the stresses undergone by these different elements, the links deteriorate in the course of time. These elements therefore have to be replaced regularly. This is an operation that entails constraints and is costly.

SUMMARY OF THE INVENTION

Hence, the technical problem to be solved by the object of the present invention is to propose a compression, device for a radiology apparatus, including a compression pad and means to fasten the pad to driving elements fitted on to the radiological apparatus, the device making it possible to obtain, at low cost, better ergonomic features than are obtained with presently existing compression devices through the elimination of the need to replace different elements of these presently existing compression devices by means of a mechanical link capable of withstanding the stresses undergone by both the compression pad and the fastening means for a lengthy period.

The approach to the technical problem raised, according to the present invention, lies in the fact that the compression pad and the fastening means constitute a single part made of an injected plastic material that is transparent to X-rays.

The compression device according to the invention forms an element consisting of a single piece, integrating the pad proper and fastening means. This set corresponds to the mechanical characteristics of bending and fatigue strength, whatever may be the shape and dimensions of the pad. A particular type of sizing of the structure is necessary for each type of pad used.

The cost of the compression device that is the object of the invention is especially advantageous since it is 20 to 30 times lower than that of present devices that use separate elements that are assembled.

Furthermore, the compression pad itself, namely the part in contact with the breast, crossed by the X-rays, is transparent and has perfect constancy of thickness, resulting from the use of the technique of injection of a plastic material which results in a homogeneity of transmission and in an image quality of radiological pictures that is far higher than that obtained with conventional thermoformed pads.

According to a particular embodiment of the invention, the plastic material is polycarbonate.

BRIEF DESCRIPTION OF THE DRAWINGS

The following description, made with reference to the appended drawings, which are given as non-restrictive examples, will give a clear idea of the content of the invention and the way in which it can be obtained.

FIG. 1 is a half view from the top of a compression device according to the invention.

FIG. 2 is a side view seen in a section along the line II—II of FIG. 1.

MORE DETAILED DESCRIPTION

The half view from the top of FIG. 1 and the side view of FIG. 2 show a compression device for a radiological apparatus including a compression pad 100 designed to rest on any organ, a breast for example, so as to hold it with the required pressure against the plate-holder (not shown) of the radiological apparatus. This compression pad 100 is essentially constituted by a part in direct contact with the organ, having the shape of a flat bottom 110, and a peripheral wall 120 surrounding the flat bottom 110. During operation, X-rays reach the organ considered through the flat bottom 110.

The device of FIGS. 1 and 2 also includes means 200 to fix the compression pad 100 to driving elements (not shown) fitted on to the radiological apparatus which are, for example, of the rack-and-pinion drive column type.

As can be seen in FIGS. 1 and 2, the compression pad 100 and the fastening means 200 constitute a single element made of injected plastic, transparent to X-rays. In the embodiment of FIGS. 1 and 2, the mechanical resistance of the fastening means 200 is provided by a structure of reinforcement pieces 210 positioned in a meshwork whose sizing takes account of the nature of the plastic used as well as the projection imposed on the fastening means by the pad 100 when the organ is compressed, the compression possibly going up to $2 \times 10^6$ Pa.

Naturally, the shape of the fastening means 200 could be different from those shown in FIGS. 1 and 2, depending essentially on the size given to the compression pad 100, the dimensions of which vary according to the organ examined.

In a particular embodiment, the plastic material is made of polycarbonate.

By molding, there are obtained compression pads whose flat bottom 110, crossed by the X-rays, shows excellent homogeneity and a constancy of thickness of some hundredths of a millimeter, with high reproducibility for pads of all shapes and sizes.

In FIG. 1, it can be seen that the compression pad 110 has a marking 111 that is transparent to X rays, enabling the marking 111 to display the positioning of a detection cell of an automatic exposure device.

What is claimed is:

1. A compression device for a radiological apparatus, said compression device comprising a compression pad and fastening means to connect said compression pad to driving elements that are fitted onto said radiological apparatus, wherein both said compression pad and said fastening means are a single unitary piece of injection molded plastic that is substantially transparent to X-rays.

2. A device according to claim 1, wherein said single unitary piece of injection molded plastic comprises a polycarbonate.

3. A device according to claim 1, wherein said fastening mean comprises a structure of reinforcement pieces positioned in a meshwork.

4. A device according to claim 1, wherein said single unitary piece of injection molded plastic comprises a flat bottom.

5. A device according to claim 4, wherein said single unitary piece of injection molded plastic further comprises a peripheral wall surrounding said flat bottom.

6. A device according to any of the claims 1 or 3-5, wherein said compression pad comprises a variable position marking that is substantially transparent to X-rays, said variable position marking displaying position of a detection cell of an automatic exposure device.

7. A compression device for a radiological apparatus, said compression device comprising a single unitary piece of injection molded plastic material comprising a compression pad and fastening means to connect said compression pad to driving elements that are fitted onto said radiological apparatus, wherein said single unitary piece of injection molded plastic is substantially transparent to X-rays.

8. A device according to claim 7, wherein said single unitary piece of injection molded plastic material comprises a polycarbonate.

9. A device according to claim 7, wherein said fastening means comprises a structure of reinforcement pieces positioned in a meshwork.

10. A device according to claim 7, wherein said single unitary piece of injection molded plastic comprises a flat bottom.

11. A device according to claim 10, wherein said single unitary piece of injection molded plastic further comprises a peripheral wall surrounding said flat bottom.

12. A device according to any one of claims 7-8 or 9-11, wherein said compression pad comprises a variable position marking that is substantially transparent to X-rays, said variable position marking displaying a position of a detection cell of an automatic exposure device.

* * * * *